United States Patent [19]

Hellring

[11] Patent Number: 5,072,031
[45] Date of Patent: * Dec. 10, 1991

[54] LAYERED DIVALENT METAL PHOSPHATES CONTAINING PENDENT SUBSTITUENT GROUPS AND THEIR PREPARATION

[75] Inventor: Stuart D. Hellring, Trenton, N.J.

[73] Assignee: Mobil Oil Corp., Fairfax, Va.

[ * ] Notice: The portion of the term of this patent subsequent to Oct. 9, 2007 has been disclaimed.

[21] Appl. No.: 550,007

[22] Filed: Jul. 9, 1990

Related U.S. Application Data

[60] Division of Ser. No. 139,240, Dec. 29, 1987, Pat. No. 4,962,228, which is a continuation-in-part of Ser. No. 23,345, Mar. 9, 1987, Pat. No. 4,846,853.

[51] Int. Cl.$^5$ ............... C01B 25/26; C01B 25/32; C01B 25/34
[52] U.S. Cl. .................. 562/8; 423/249; 423/305; 423/306; 423/308; 423/309; 423/592; 423/593; 423/601; 423/602; 423/617; 423/622; 423/635; 423/636; 534/10; 556/19; 556/30; 556/43; 556/76
[58] Field of Search .............. 562/8; 423/308, 309, 423/249, 305, 306, 592, 593, 601, 602, 617, 622, 635, 636; 534/10; 556/19, 30, 43, 76

[56] References Cited

U.S. PATENT DOCUMENTS 4,846,853  7/1989  Chang et al. .................. 423/309
4,962,228  10/1990  Hellring ........................ 562/8

Primary Examiner—Wayne A. Langel
Attorney, Agent, or Firm—Alexander J. McKillop; Charles J. Speciale; Edward F. Kenehan, Jr.

[57] ABSTRACT

Layered divalent metal pentavalent metallate, $M(HAO_4)_x(RAO_3)_y(Z)_z$ wherein M is divalent metal, A is a pentavalent metal, e.g. phosphorus, R is a substituent group other than H or OH, e.g., phenyl, covalently bonded to A, $x+y=1$, y is greater than 0, z ranges from 0 to 2, inclusive, and Z is an intercalated moiety is prepared by contacting a source of divalent metal with a substituted phosphonic acid-type compound under hydrothermal conditions.

19 Claims, 2 Drawing Sheets

LAYERED DIVALENT METAL PHOSPHATES CONTAINING PENDENT SUBSTITUENT GROUPS AND THEIR PREPARATION

This application is a division of U.S. application Ser. No. 139,240, filed Dec. 29, 1987, now U.S. Pat. No. 4,962,228, which is a continuation-in-part of U.S. application Ser. No. 023,345, filed March 9, 1987, now U.S. Pat. No. 4,846,853. The entire contents of these applications are incorporated herein by reference.

This invention relates to a layered metal hydrogen phosphate-type composition $M(HAO_4)_x(RAO_3)_y(Z)_z$ wherein M is an element selected from the group consisting of Group IIA and Group IIB elements, A is a pentavalent metal, e.g., P, R is a substituent other than H or OH, which is covalently bonded to A, Z is a moiety intercalated between the layers of the composition, e.g., $H_2O$, $x+y=1$, y is greater than 0, and z ranges from about 0 to 2. The invention further relates to a method of preparing the layered composition. In one particularly preferred embodiment of this invention, M is magnesium.

Many layered materials are known which have three-dimensional structures which exhibit their strongest chemical bonding in only two dimensions. In such materials, the stronger chemical bonds are formed in two-dimensional planes and a three-dimensional solid is formed by stacking such planes on top of each other. However, the interactions between the planes are weaker than the chemical bonds holding an individual plane together. The weaker bonds generally arise from interlayer attractions such as Van der Waals forces, electrostatic interactions, and hydrogen bonding. In those situations where the layered structure has electronically neutral sheets interacting with each other solely through Van der Waals forces, a high degree of lubricity is manifested as the planes slide across each other without encountering the energy barriers that arise with strong interlayer bonding. Graphite is an example of such a material. The silicate layers of a number of clay materials are held together by electrostatic attraction mediated by ions located between the layers. In addition, hydrogen bonding interactions can occur directly between complementary sites on adjacent layers, or can be mediated by interlamellar bridging molecules, e.g., water.

Among these layered materials ar those containing corner-sharing $PO_2$ and $TO_2$ tetrahedra wherein T is a non-phosphorus trivalent atom. For example $GaPO_4 \cdot 2H_2O$ (*Acta Crysta.*, 1966, 20, 520) has been reported as having been prepared under hydrothermal conditions. Other trivalent phosphates include $InPO_4 \cdot 2H_2O$ (*Acta Crysta.*, 1961, 14, 1140) and $AlPO_4 \cdot 2H_2O$'s, variscite (*Acta Crysta.*, 1977, B33, 263) and metavariscite (*Acta Crysta.*, 1973, B29, 2292). However, such trivalent cationic phosphates are not expected to exhibit any ion exchange capabilities since they possess an electrovalently neutral framework. Layered tetravalent cationic phosphates, e.g., crystalline zirconium phosphates $Zr(HPO_4)_2$ and $Zr(HPO_4)_2 \cdot 2H_2O$ having a major X-ray reflection peak at 7.56A to 8.0A are disclosed in U.S. Pat. No. 3,416,884 along with methods of preparation and ion exchange properties.

U.S. patent application Ser. No. 023,345, filed Mar. 9, 1987 discloses a layered divalent metal hydrogen phosphate material which is believed to contain corner-sharing $PO_2$ and $MO_2$ tetrahedra, wherein M is a divalent metal selected from the group consisting of Group IIA and Group IIB elements of the Periodic Table. The formula for these materials can be written as $MHPO_4 \cdot nZ$, wherein n ranges from about 0 to 2 and Z is an intercalated moiety. In the hydrated form, $Z=H_2O$. The extent of hydration in the material can depend upon the synthesis conditions employed. Moreover, the monohydrate form (n=1) can be dehydrated to the anhydrous form (n=0) by careful exposure to dehydrating conditions. When these materials are exposed to higher temperatures, e.g., above 250° C., another 0.5 mole of water is irreversibly desorbed from the framework due to pyrophosphate formation and subsequent collapse to the dense phase is indicated by an X-ray diffraction pattern d-spacing of less than about 6 angstroms.

Figure 1:
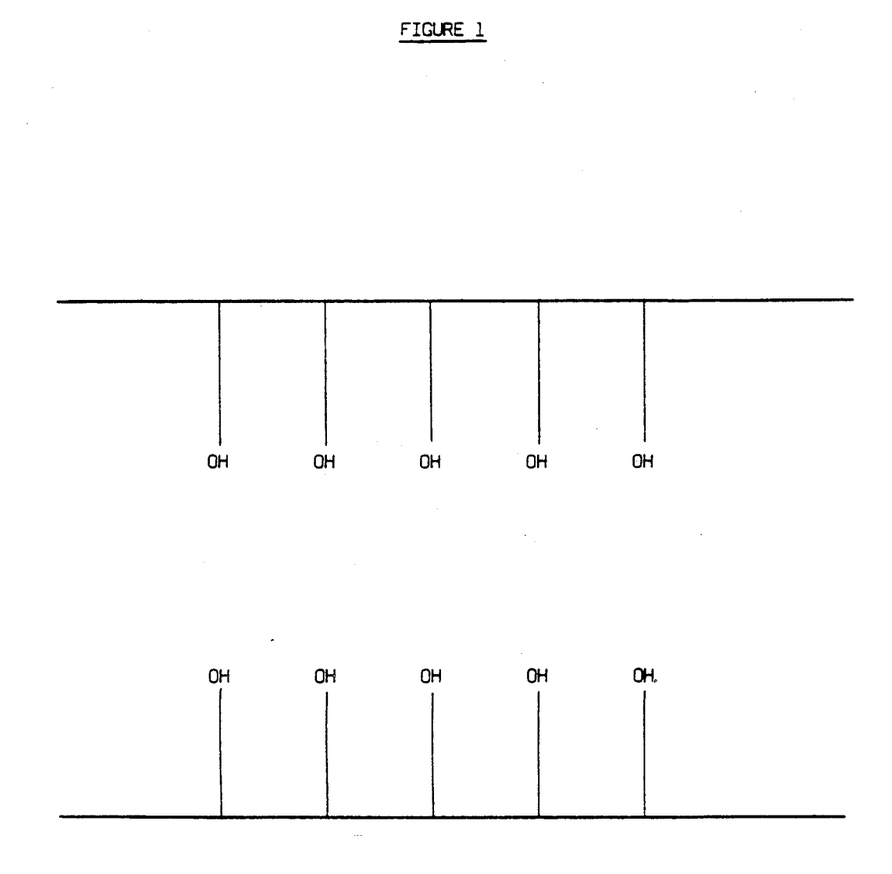
FIG. 1 depicts the arrangement of pendent groups of a layered divalent metal hydrogen phosphate.
Figure 2:
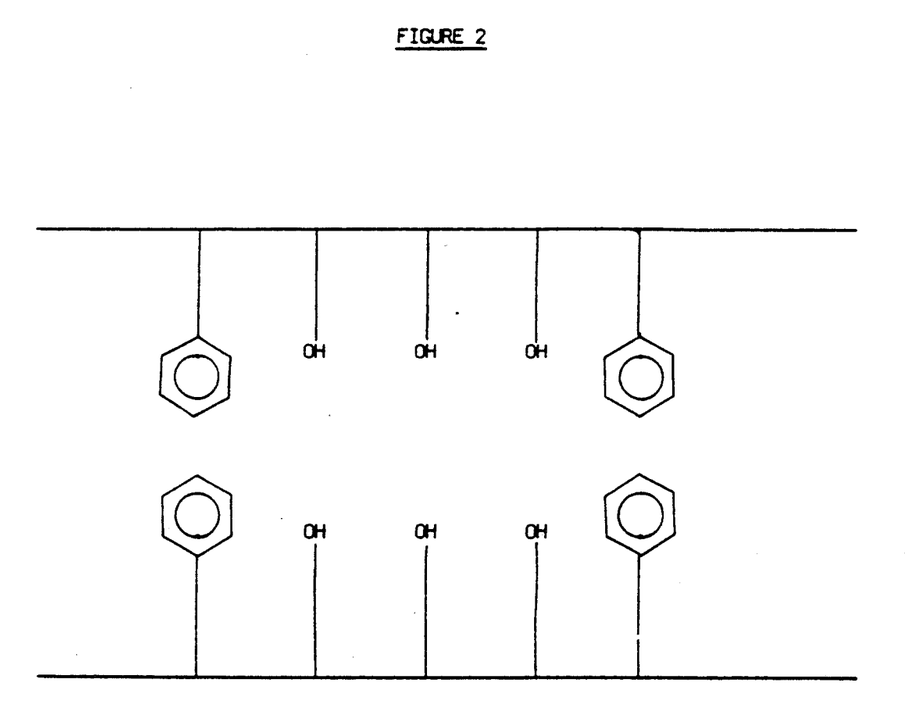
FIG. 2 depicts the arrangement of pendent groups, including substituent R groups, in a layered divalent metal phosphate of the present invention.

The present invention involves a method for preparing related materials which enjoy an enhanced interlayer distance owing to the presence of non-hydroxyl pendent substituents. As can be seen in FIG. 1, materials disclosed in U.S. application Ser. No. 023,345, are believed to comprise layers having pendent hydroxyl groups projecting into the interlayer space. It has now been found that a similar material which contains at least some pendent groups other than pendent hydroxyl or hydrogen can be prepared. Said pendent groups can be formed in situ during crystallization of the layered material. FIG. 2 depicts such an arrangement of pendent groups in the layered material.

The chemical formula of the materials of the present invention can be written as $M(HAO_4)_x(RAO_3)_y(Z)_z$ wherein M is a divalent metal selected from the Group consisting of Group IIA and Group IIB elements of the Periodic Table, i.e., Be, Mg, Ca, Sr, Ba and Ra; and Zn, Cd, and Hg, respectively, preferably Group IIA metals, A is a pentavalent metal atom, such as phosphorus, covalently bonded by an oxygen linkage to divalent metal atom M. R is a group covalently bonded to A in $RAO_3$, other than hydroxyl or hydrogen, e.g. an organic group, Z is an intercalated moiety, $x+y=1$, y is greater than 0, preferably greater than about 0.1 or more preferably greater than about 0.25, and z ranges from 0 to about 2, inclusive.

Moieties independent of the pendent group, represented by Z, such as $H_2O$ can be intercalated between the layers. Other suitable moieties can include organics such as amines and alcohols. Hydrolyzable compounds such as organometallics can be introduced to the layered material and reacted with residual or added water to form metal oxide pillars. Moreover, ions may be intercalated within the layered material to form ion intercalated compositions.

For convenience herein, the description of the invention will be described with regard to phosphorus and its selection as the pentavalent metal. However, it is to be understood that the other pentavalent metals can be used and the description with regard to phosphorus will generally also apply analogously to the other pentavalent metals, for example, arsenic, antimony, vanadium, niobium and tantalum. The term "pentavalent metals" is used herein to describe the above pentavalent atoms which are metals or have metal-like properties; phosphorus, although not a true metal, is herein considered to be metal-like and included within the definition. With regard to selecting arsenic as the pentavalent metal, the general description herein of phosphorus is analogous because an arsine is analogous to a phosphine, an arsenate to a phosphate, an arsonate to a phosphonate, an arsinate to a phosphinate, an arsenic compound to a phosphorus compound, an arsenic compound to a phosphonic compound, an arsenic acid to phosphoric acid, and an arsenious acid to phosphorous acid.

The process of preparation comprises a liquid media reaction, preferably aqueous, in which at least one substituted pentavalent metal acid of the formula ((HO)-$_2$OA) R having a phosphonate-type structure wherein R is a ligand other than H or OH, is reacted with at least one divalent metal ion. Optionally, the reaction mixture can contain an additional source of hydrogen, an additional source of A and/or an additional source of oxygen. Ortho-phosphoric and/or phosphorous acid (P(OH)$_3$) and their pentavalent analogues can be present as the optional source of their constituent elements.

In one preferred embodiment, ortho-phosphoric acid is a component of the reaction mixture. The molar ratio of substituted phosphoric acid to ortho-phosphoric acid in the reaction mixture can range from at least about 0.1, preferably at least about 0.25. Reaction preferably occurs in the presence of an excess of the phosphorus acid compound and the metal ion is provided as a compound soluble in the liquid media. The normal liquid media is water. However, organic solvents, particularly ethanol, can be employed where water will interfere with the desired reaction.

The molar ratio of divalent metal to pentavalent metal can range from about 0.8 to about 1.2, preferably from about 0.95 to 1.05, say about 1. Sources of divalent metal include a soluble salt MX$_2$ where X is the anion of the salt. X can be selected from the group of anions including halides, $HSO_4^{-1}$, $SO_4^{-2}$, $O_2C-CH_3^{-1}$, $NO_3^{-1}$, $O^{-2}$, and $OH^{-1}$, with oxides and hydroxides preferred.

By the term "substituted phosphorus acid compound," as used herein, there is meant a compound of the formula: ((HO)$_2$OPR wherein n is 1 or 2, R is any group which will replace a hydroxyl of phosphoric acid and/or the hydrogen of phosphorous acid and couple to the acid by a covalent bond. Coupling to the acid may be through carbon, oxygen, silicon, sulfur, nitrogen and the like. Coupling through carbon or an oxygen-carbon group is presently preferred. When coupling is through carbon, the substituted phosphorus acid compound is an organophosphonic acid and the product a phosphonate. When coupling is through oxygen-carbon, the substituted phosphorus acid compound is an organophosphoric monoester acid and the product a phosphate.

As used herein, R can be an acyclic group, heteroacyclic group, alicyclic group, aromatic group or heterocyclic group as well as an organometallic group.

The term "acyclic group," as used herein, means a substituted or unsubstituted acyclic group. The term "acyclic" includes saturated and unsaturated aliphatics which can be straight chain or branched chain. The "aliphatics" include alkyl, alkenyl and alkynyl.

The term "heteroacyclic group," as used herein, means an acyclic group containing one or more heteroatoms in the chain selected from oxygen, nitrogen and sulfur. The heteroatoms can be the same or different in each chain and usually the number of heteroatoms is one, two or three.

The term "alicyclic group," as used herein, means a substituted or unsubstituted alicyclic group. The term "alicyclic" includes saturated and unsaturated cyclic aliphatics.

The term "aromatic groups" as used herein, means a substituted or unsubstituted aromatic group. The term "aromatic" includes phenyl, naphthyl, biphenyl, anthracyl and phenanthryl. Phenyl is a preferred aromatic.

The term "heterocyclic group," as used herein, means a substituted or unsubstituted heterocyclic group. The term "heterocyclic" means an alicyclic or aromatic group containing one or more heteroatoms in the ring selected from oxygen, nitrogen and sulfur. The heteroatom can be the same or different in each ring and usually the number of heteroatoms is one, two or three.

The terms "substituted acyclic," "substituted heteroacyclic," "substituted alicyclic," "substituted aromatic" and "substituted heterocyclic," as used herein, mean an acyclic, heteroacyclic, alicyclic, aromatic or heterocyclic group substituted with one or more of the groups selected from alkyl, alkenyl, alkynyl, alkoxy, alkenyloxy, alkynyloxy, alkylthio, alkenythio, alkynylthio, halo, oxo, hydroxy, carbonyl, carboxy, alkylcarbonylloxy, alkylcarbonyl, carboxyalkyl, thio, mercapto, sulfinyl, sulfonyl, imino, amino, cyano, nitro, hydroxyamine, nitroso, cycloalkyl, cycloalkalkyl, aryl, aralkyl, alkaryl, aryloxy, arylalkoxy, alkaryloxy, arylthio, aralkylthio, alkarylthio, arylamino, aralkylamine and alkarylamino.

In addition, R can be an inorganic radical group other than —H or —OH. Examples of such groups include alkoxy, aryloxy, amino, organosilyl and thionyl.

The size of R can affect the interlayer distance of the resulting layered product. For example, as little as 10-25% phenylphosphonic acid incorporated into the hydrothermal preparation, i.e., y=0.10 to 0.25, results in a 4 to 5 angstrom increase in interstitial distance (as exhibited by X-ray diffraction) over the analogous material which does not have pendent phenyl groups in the interlayer space. In addition, enhanced thermal stability can be observed, even where the pendent groups of the layered material are organic.

The compositions of the present invention, containing pendent groups other than H or OH in the interlayer space, are preferably prepared by a method which comprises hydrothermally treating an aqueous mixture having an initial pH prior to said treatment ranging from about 3 to 10. The aqueous mixture contains a source of at least one divalent metal M, and a substituted phosphonic acid.

The initial pH of the aqueous reaction mixture is preferably between about 5 to 9, even more preferably between about 6 to 8 say between 6.5 and 7.5. The initial pH of the aqueous mixture can be raised or lowered, if necessary, to place it within the desired range by addition of a pH-altering material to the aqueous mixture. Phosphoric acid is an especially useful additive for lowering the initial pH of the aqueous mixture, while amines or organic ammonium compounds, e.g., dipropylamine, triethylamine and tetraethylammonium hydroxide, can be employed to raise the pH to desired levels. pH raising materials which are incapable of adjusting reaction mixture without forming a salt of a pentavalent salt, e.g. a phosphate salt are particularly useful. Generally, when phosphoric acid is used as the phosphorus source, the pH of the mixture is highly acidic and requires addition of a pH-raising material in order to achieve the desired initial pH.

The hydrothermal conditions employed in obtaining the layered compositions of the present invention include temperatures of about 50° to 500° C., preferably about 100 to 250° C., pressures of about 345 to 3450 kPa, preferably about 690 to 1725 kPa and contact times of about 5 to 192 hours, preferably about 12 to 72 hours, or until such times as crystals of the layered compositions are formed.

The materials of the present invention which contain an intercalated moiety (exclusive of the pendent group), i.e., n is greater than zero, contain a three-dimensional channel between adjacent layers in which the intercalated moiety, e.g., water is present. Materials of the present invention containing pendent substituents which are thermally stable may be useful in catalysts or catalyst supports employed in chemical conversions at elevated temperatures.

The extent of interlayer separation of the present compositions can be estimated by using standard techniques such as X-ray diffraction using CuK radiation to determine the basal spacing, also known as "repeat distance" or "d-spacing." These values indicate the distance between, for example, the uppermost margin of one layer with the uppermost margin of its adjoining layer. If the layer thickness is known, the interlayer spacing can be determined by subtracting the layer thickness from the basal spacing.

The following examples are given to further describe the present invention. D-spacings are given in angstroms. "Mol.%'s" described in the examples refers to "in-preparation values" and may only approximate values in final product.

EXAMPLE 1

Magnesium oxide powder (9.65 g) was added to a solution of ortho-phosphoric acid (27.6 g) in water (55 g) while the exothermic mixture was hand stirred. The acidic mixture was adjusted from a pH of 3 to a pH of 7.2 with dipropylamine (7.55 g) and heated to 180° C. in a teflon-lined autoclave under nitrogen pressure (230 psig) while stirring. After 4 days, the mixture (pH =6.2) was cooled, centrifuged, filtered, and washed with water. After drying (110° C. for 2 hr), the product was recovered as a white powder (30.3 g) which showed the following X-ray diffraction pattern:

| PEAK | D-SPACE | RELATIVE INTENSITY |
| --- | --- | --- |
| 1 | 10.98 | 100.0 |
| 2 | 8.73 | 30.4 |
| 3 | 7.22 | 12.9 |
| 4 | 6.54 | 32.3 |
| 5 | 6.10 | 9.6 |
| 6 | 5.33 | 66.4 |
| 7 | 4.90 | 4.0 |
| 8 | 4.53 | 3.3 |
| 9 | 4.28 | 5.7 |
| 10 | 4.22 | 5.4 |
| 11 | 4.07 | 7.5 |
| 12 | 4.03 | 4.7 |
| 13 | 3.84 | 21.7 |
| 14 | 3.79 | 12.4 |
| 15 | 3.54 | 20.0 |
| 16 | 3.33 | 9.6 |
| 17 | 3.24 | 42.0 |
| 18 | 3.19 | 7.6 |
| 19 | 3.13 | 4.5 |
| 20 | 3.07 | 23.6 |
| 21 | 3.03 | 22.4 |
| 22 | 2.93 | 18.4 |
| 23 | 2.90 | 13.2 |
| 24 | 2.87 | 25.0 |
| 25 | 2.84 | 17.5 |
| 26 | 2.71 | 15.3 |
| 27 | 2.66 | 12.8 |
| 28 | 2.61 | 5.5 |
| 29 | 2.58 | 9.3 |

EXAMPLE 2

Magnesium oxide powder (9.65 g) was added to a solution of ortho-phosphoric acid (OPA) (20.9 g) and phenylphosphonic acid (PPA) (9.48 g) in water (55 g) while the mixture was hand stirred (exothermic). The ratio of PPA to OPA was about 1 to 3. The acidic, sudsy mixture was adjusted from pH =3 to pH =7.2 with dipropylamine (10.9 g) and heated to 180° C. in a teflon-lined autoclave under nitrogen pressure (230 psig) while stirring. After 4 days, the mixture (pH=6.2) was cooled, centrifuged, filtered, and washed with water. After drying (110° C. for 2 hr), the product was recovered as a white powder (29.2 g) which showed the following X-ray diffraction pattern:

| PEAK | D-SPACE | RELATIVE INTENSITY |
| --- | --- | --- |
| 1 | 14.45 | 100.00 |
| 2 | 8.72 | 64.90 |
| 3 | 7.22 | 23.50 |
| 4 | 6.54 | 20.00 |
| 5 | 5.25 | 16.88 |
| 6 | 4.90 | 18.09 |
| 7 | 4.60 | 19.29 |
| 8 | 4.22 | 21.07 |
| 9 | 3.84 | 23.18 |
| 10 | 3.80 | 23.44 |
| 11 | 3.68 | 24.21 |
| 12 | 3.60 | 24.72 |
| 13 | 3.19 | 27.98 |
| 14 | 3.12 | 28.60 |
| 15 | 3.03 | 29.50 |
| 16 | 2.90 | 30.82 |
| 17 | 2.88 | 31.09 |
| 18 | 2.84 | 31.53 |
| 19 | 2.71 | 33.04 |
| 20 | 2.66 | 33.64 |
| 21 | 2.58 | 34.75 |

This shows that incorporating 25 mol.% phenylphosphonic acid into the preparation increases the interstitial spacing by over 3A. The product in Example 2 is further distinguished from that in Example 1 by a rapid weight loss in thermogravimetric analysis (TGA) conducted at 20° C./minute, 200 ml He/minute with a maximum rate near 650° C., which is not present with the product of Example 1. This weight loss is probably due to decomposition of the phenylphosphonate linkage.

The thermal stability of the product from Example 2 was demonstrated by heating separate gram samples to 100°, 200°, 300°, 400°, and 500° C., each at a rate adjusted to reach final temperature in 45 min., then held 5 min. at this temperature (FIG. 2). Collapse of the low angle peak (d=14.39) was significant in the sample heated to 400° C., and complete at 500° C. The sample was stable at 300° C. which shows that the substitution of R for pendent OH stabilizes the interstitial distances by at least 100° C. over Example 1 which begins to collapse above 200° C.

EXAMPLE 3

Magnesium oxide powder (4.82 g) was added to a solution of phenylphosphonic acid (19.0 g) in water (40.5 g) while the mixture was hand stirred (exothermic). The acidic mixture was adjusted from pH=2 to pH=7.2 with dipropylamine (4.88 g) and heated to 180° C. in a teflon-lined 300 ml autoclave under nitrogen pressure (200 psig) while stirring. Due to excess volume, 23.8 g of this mixture was not added to the autoclave. After 4 days, the mixture was cooled, centrifuged, filtered, and washed with water. After drying (110° C. for 2 hr), the product was recovered as a white powder (17.4 g) which showed the following X-ray diffraction pattern:

| PEAK | D-SPACE | I/IMAX |
| --- | --- | --- |
| 1 | 16.278 | 2.6 |
| 2 | 15.909 | 3.9 |
| 3 | 14.900 | 16.3 |
| 4 | 14.427 | 100.0 |
| 5 | 7.319 | 1.7 |
| 6 | 7.193 | 11.7 |
| 7 | 5.375 | 0.4 |
| 8 | 5.252 | 14.8 |
| 9 | 4.824 | 0.6 |
| 10 | 4.783 | 1.6 |
| 11 | 4.789 | 1.7 |
| 12 | 4.602 | 9.1 |
| 13 | 4.189 | 0.1 |
| 14 | 4.097 | 0.1 |
| 15 | 4.047 | 0.7 |
| 16 | 4.033 | 1.4 |
| 17 | 4.023 | 1.8 |
| 18 | 3.676 | 4.1 |
| 19 | 3.650 | 2.4 |
| 20 | 3.592 | 4.0 |
| 21 | 3.467 | 0.2 |
| 22 | 3.409 | 2.2 |
| 23 | 3.356 | 0.1 |
| 24 | 3.284 | 0.7 |
| 25 | 3.276 | 1.1 |
| 26 | 3.111 | 0.4 |
| 27 | 3.106 | 0.5 |
| 28 | 3.098 | 0.5 |
| 29 | 3.066 | 0.2 |
| 30 | 3.040 | 0.2 |
| 31 | 3.024 | 0.3 |
| 32 | 2.965 | 0.1 |
| 33 | 2.956 | 0.1 |
| 34 | 2.916 | 3.9 |
| 35 | 2.882 | 2.0 |
| 36 | 2.874 | 2.3 |
| 37 | 2.872 | 2.5 |
| 38 | 2.872 | 1.5 |
| 39 | 2.843 | 0.1 |
| 40 | 2.821 | 1.1 |
| 41 | 2.817 | 2.0 |
| 42 | 2.816 | 1.4 |
| 43 | 2.765 | 0.8 |
| 44 | 2.764 | 0.8 |
| 45 | 2.637 | 0.1 |
| 46 | 2.621 | 0.1 |
| 47 | 2.571 | 2.5 |

These data show that no increase in interstitial spacing was obtained between 25 mol.% and 100 mol.% PPA in the magnesium preparation.

EXAMPLE 4

Magnesium oxide powder (9.65 g) was added to a solution of ortho-phosphoric acid (24.9 g) and phenylphosphonic acid (3.79 g) in water (55 g) while the mixture was hand stirred (exothermic). The acidic mixture was adjusted from pH=3 to pH=7.2 with dipropylamine (11.67 g) and heated to 180° C. in a teflon-lined autoclave under nitrogen pressure (210 psig) while stirring. After 4 days, the mixture was cooled, centrifuged, filtered, and washed with water. After drying (110° C. for 2 hr), the product was recovered as a white powder (28.5 g) which showed the following X-ray diffraction pattern:

| PEAK | D-SPACE | RELATIVE INTENSITY |
| --- | --- | --- |
| 1 | 8.740 | 100.0 |
| 2 | 7.228 | 25.2 |
| 3 | 6.548 | 42.3 |
| 4 | 5.960 | 25.6 |
| 5 | 5.354 | 28.9 |
| 6 | 4.906 | 5.8 |
| 7 | 4.723 | 38.6 |
| 8 | 4.620 | 4.6 |
| 9 | 4.504 | 10.7 |
| 10 | 4.219 | 8.2 |
| 11 | 4.153 | 11.9 |
| 12 | 3.840 | 33.7 |
| 13 | 3.798 | 5.4 |
| 14 | 3.657 | 8.4 |
| 15 | 3.469 | 26.2 |
| 16 | 3.191 | 17.0 |
| 17 | 3.091 | 15.0 |
| 18 | 3.042 | 42.7 |
| 19 | 3.031 | 44.5 |
| 20 | 2.903 | 32.7 |
| 21 | 2.878 | 24.9 |
| 22 | 2.839 | 26.7 |
| 23 | 2.795 | 11.1 |
| 24 | 2.726 | 10.3 |
| 25 | 2.711 | 8.4 |
| 26 | 2.584 | 34.2 |

These data show that 10 mol.% PPA was insufficient to effect pillaring in the final product.

EXAMPLE 5

Calcium oxide powder (13.46 g) was added to a solution of ortho-phosphoric acid (27.6 g) in water (55 g) while the mixture was hand stirred (exothermic). The acidic mixture was adjusted from pH=2 to pH=7.2 with dipropylamine (5.92 g) and heated to 180° C. in a teflon-lined autoclave under nitrogen pressure (260 psig) while stirring. After 4 days, the mixture was cooled, centrifuged, filtered, and washed with water. After drying (110° C. for 2 hr), the product was recovered as a white powder (24.3 g) which showed the following X-ray diffraction pattern:

| PEAK | D-SPACE | RELATIVE INTENSITY |
| --- | --- | --- |
| 1 | 3.443 | 17.6 |
| 2 | 3.376 | 100.0 |
| 3 | 3.358 | 81.9 |
| 4 | 3.128 | 17.5 |
| 5 | 3.090 | 9.2 |
| 6 | 2.960 | 87.4 |
| 7 | 2.937 | 31.1 |
| 8 | 2.818 | 39.3 |
| 9 | 2.781 | 18.6 |
| 10 | 2.757 | 36.0 |
| 11 | 2.727 | 62.0 |

These data show that a rather dense crystalline phase is obtained without PPA present in the calcium preparation.

EXAMPLE 6

Calcium oxide powder (9.65 g) was added to a solution of ortho-phosphoric acid (20.9 g) and phenylphosphonic acid (9.48 g) in water (55 g) while the mixture was hand stirred (exothermic). The sudsy, acidic mixture was adjusted from pH=2 to pH=7.2 with dipropylamine (6.18 g) and heated to 166° C. in a teflon-lined autoclave under nitrogen pressure (205 psig) while stirring. After 4 days, the mixture (pH=6.2) was cooled, centrifuged, filtered, and washed with water. After drying (110° C. for 2 hr), the product was recovered as a white powder (22.6 g) which showed the following X-ray diffraction pattern:

| PEAK | D-SPACE | RELATIVE INTENSITY |
|---|---|---|
| 1 | 35.396 | 0.1 |
| 2 | 30.983 | 0.1 |
| 3 | 28.224 | 0.0 |
| 4 | 25.952 | 0.1 |
| 5 | 15.699 | 11.0 |
| 6 | 15.407 | 100.0 |
| 7 | 11.330 | 0.1 |
| 8 | 7.703 | 4.3 |
| 9 | 6.749 | 0.6 |
| 10 | 5.278 | 0.4 |
| 11 | 5.247 | 0.7 |
| 12 | 5.133 | 4.7 |
| 13 | 4.404 | 0.2 |
| 14 | 3.929 | 0.8 |
| 15 | 3.892 | 1.0 |
| 16 | 3.850 | 17.9 |
| 17 | 3.846 | 12.6 |
| 18 | 3.444 | 2.7 |
| 19 | 3.376 | 4.6 |
| 20 | 3.359 | 3.9 |
| 21 | 3.351 | 2.5 |
| 22 | 3.300 | 0.3 |
| 23 | 3.176 | 0.7 |
| 24 | 3.145 | 0.4 |
| 25 | 3.129 | 0.9 |
| 26 | 3.091 | 1.2 |
| 27 | 3.079 | 1.7 |
| 28 | 2.962 | 3.7 |
| 29 | 2.939 | 1.4 |
| 30 | 2.818 | 6.3 |
| 31 | 2.816 | 5.0 |
| 32 | 2.783 | 3.5 |
| 33 | 2.777 | 2.6 |
| 34 | 2.762 | 1.5 |
| 35 | 2.756 | 1.7 |
| 36 | 2.724 | 5.4 |
| 37 | 2.634 | 1.4 |
| 38 | 2.620 | 0.6 |
| 39 | 2.590 | 0.4 |

The thermal stability of this product was demonstrated by heating separate gram samples to 100°, 200°, 300°, 400°, and 500° C., each at a rate adjusted to reach final temperature in 45 min., then held 5 min. at this temperature. Collapse of the low angle peak (d=15.41) was complete in the sample heated to 400° C., although the sample was stable at 300° C.

Decomposition of this product by TGA showed weight losses very similar to that of Example 5 despite their very different X-ray powder patterns. Phosphorous-31 magic-angle-spinning (mas) nmr indicated this product contained little or no organically-substituted phosphorus. However, repeating this preparation using 50 and 75 mol.% PPA gave products showing both low-temperature dehydration and high-temperature organic decomposition by TGA similar to the magnesium examples described above. These higher PPA preparations also gave X-ray diffraction patterns similar to Example 7 (100 mol.% PPA), which showed only organically-substituted phosphorous by mas nmr.

EXAMPLE 7

Calcium oxide powder (13.46 g) was added to a solution of phenylphosphonic acid (37.9 g) in water (130 g) while the mixture was hand stirred (exothermic). The acidic mixture was adjusted from pH=5.2 to pH=7.2 with dipropylamine (20.38 g) and heated to 180° C. in a teflon-lined autoclave (300 ml) under nitrogen pressure (240 psig) while stirring. Due to excess volume, 65.8 g of this mixture could not be added to the reactor. After 4 days, the mixture was cooled, centrifuged, filtered, and washed with water. After drying (110° C. for 2 hr), the product was recovered as a white powder (26.2 g) which showed the following X-ray diffraction pattern:

| PEAK | D-SPACE | RELATIVE INTENSITY |
|---|---|---|
| 1 | 19.663 | 0.2 |
| 2 | 17.808 | 1.1 |
| 3 | 16.135 | 7.0 |
| 4 | 15.948 | 10.4 |
| 5 | 14.964 | 100.0 |
| 6 | 7.586 | 2.5 |
| 7 | 7.439 | 7.8 |
| 8 | 7.460 | 8.1 |
| 9 | 7.275 | 0.5 |
| 10 | 7.211 | 0.3 |
| 11 | 4.989 | 3.7 |
| 12 | 4.971 | 4.5 |
| 13 | 4.964 | 4.8 |
| 14 | 4.830 | 0.5 |
| 15 | 4.778 | 0.8 |
| 16 | 4.719 | 1.0 |
| 17 | 4.674 | 1.0 |
| 18 | 4.618 | 0.5 |
| 19 | 4.547 | 0.2 |
| 20 | 4.120 | 0.4 |
| 21 | 3.755 | 0.2 |
| 22 | 3.727 | 0.5 |
| 23 | 3.722 | 0.5 |
| 24 | 3.709 | 0.4 |
| 25 | 3.644 | 0.2 |
| 26 | 3.585 | 0.3 |
| 27 | 3.575 | 0.4 |
| 28 | 3.566 | 0.4 |
| 29 | 3.540 | 0.3 |
| 30 | 3.442 | 0.2 |
| 31 | 3.432 | 0.3 |
| 32 | 3.098 | 0.2 |
| 33 | 3.066 | 0.2 |
| 34 | 3.056 | 0.2 |
| 35 | 3.044 | 0.4 |
| 36 | 3.037 | 0.4 |
| 37 | 2.992 | 0.3 |
| 38 | 2.982 | 0.3 |
| 39 | 2.979 | 0.3 |
| 40 | 2.972 | 0.3 |
| 41 | 2.964 | 0.2 |
| 42 | 2.956 | 0.2 |
| 43 | 2.926 | 0.2 |
| 44 | 2.918 | 0.2 |

These data show that the organically-pillared calcium phosphates are crystallographically distinct from the 25 mol.% PPA preparation described in Example 6, even though their interlaminar spacings may be similar. Data in Examples 6 and 7 also indicate that somewhat greater than 25 mol.% PPA is required to effect organic-pillaring in calcium phosphates.

EXAMPLE 8

Calcium oxide powder (13.46 g) was added to a solution of ortho-phosphoric acid (24.9 g) and phenylphosphonic acid (3.79 g) in water (55 g) while the mixture was hand stirred (exothermic). The acidic mixture was adjusted from pH=3 to pH=7.2 with dipropylamine (6.52 g) and heated to 180° C. in a teflon-lined autoclave under nitrogen pressure (220 psig) while stirring. After 4 days, the mixture (pH=6.2) was cooled, centrifuged, filtered, and washed with water. After drying (110° C. for 2 hr), the product was recovered as a white powder (25.1 g) which showed the following X-ray diffraction pattern:

| PEAK | D-SPACE | RELATIVE INTENSITY |
|---|---|---|
| 1 | 32.386 | 2.4 |
| 2 | 26.788 | 0.5 |
| 3 | 20.512 | 2.9 |
| 4 | 19.303 | 1.2 |
| 5 | 8.195 | 8.2 |
| 6 | 6.757 | 24.6 |
| 7 | 3.488 | 45.0 |
| 8 | 3.375 | 88.4 |
| 9 | 3.356 | 48.2 |
| 10 | 3.301 | 8.9 |
| 11 | 3.234 | 1.6 |
| 12 | 3.190 | 10.9 |
| 13 | 3.172 | 11.8 |
| 14 | 3.128 | 20.7 |
| 15 | 2.961 | 100.0 |
| 16 | 2.939 | 35.2 |
| 17 | 2.887 | 9.1 |
| 18 | 2.868 | 16.3 |
| 19 | 2.818 | 89.0 |
| 20 | 2.818 | 76.3 |
| 21 | 2.780 | 52.3 |
| 22 | 2.764 | 31.6 |
| 23 | 2.758 | 37.5 |
| 24 | 2.729 | 76.4 |
| 25 | 2.634 | 16.1 |
| 26 | 2.632 | 18.1 |
| 27 | 2.625 | 9.6 |
| 28 | 2.595 | 5.4 |
| 29 | 2.580 | 1.3 |

These data show that 10 mol.% PPA was insufficient to effect pillaring in the calcium preparation.

EXAMPLE 9

Barium oxide powder (36.8 g) was added to a solution of ortho-phosphoric acid (27.6 g) in water (55 g) while the mixture was hand stirred (exothermic). The acidic mixture was adjusted from pH=1 to pH=7.1 with dipropylamine (12.1 g) and heated to 175° C. in a teflon-lined autoclave under nitrogen pressure (200 psig) while stirring. After 3 days, the mixture (pH=10) was cooled, centrifuged, filtered, and washed with water. After drying (110° C. for 2 hr), the product was recovered as a white powder (53.3 g) which showed the following X-ray diffraction pattern:

| PEAK | D-SPACE | RELATIVE INTENSITY |
|---|---|---|
| 1 | 4.441 | 31.4 |
| 2 | 3.861 | 14.3 |
| 3 | 3.588 | 100.0 |
| 4 | 3.528 | 41.5 |
| 5 | 3.196 | 10.2 |
| 6 | 3.001 | 25.1 |
| 7 | 2.855 | 30.7 |
| 8 | 2.804 | 11.1 |

These data show that a relatively dense phase is obtained without PPA pillaring in the barium preparation.

EXAMPLE 10

Barium oxide powder (36.8 g) was added to a solution of ortho-phosphoric acid (20.9 g) and phenylphosphonic acid (9.48 g) in water (55 g) while the mixture was hand stirred (exothermic). The acidic mixture was adjusted from pH=3 to pH=7.3 with dipropylamine (0.55 g) and heated to 180° C. in a teflon-lined autoclave under nitrogen pressure (210 psig) while stirring. After 4 days, the mixture (pH=7.0) was cooled, centrifuged, filtered, and washed with water. After drying (110° C. for 2 hr), the product was recovered as a white powder (48.4 g) which showed the following X-ray diffraction pattern:

| PEAK | D-SPACE | RELATIVE INTENSITY |
|---|---|---|
| 1 | 15.892 | 17.0 |
| 2 | 4.734 | 9.9 |
| 3 | 4.440 | 29.4 |
| 4 | 3.862 | 15.7 |
| 5 | 3.589 | 100.0 |
| 6 | 3.528 | 45.7 |
| 7 | 3.181 | 61.5 |
| 8 | 3.001 | 25.9 |
| 9 | 2.855 | 26.8 |
| 10 | 2.802 | 58.4 |

EXAMPLE 11

Barium oxide powder (36.8 g) was added to a solution of phenylphosphonic acid (37.8 g) in water (105 g while the mixture was hand stirred (exothermic). The basic, gritty mixture (pH=11-12) was heated to 185° C. in a teflon-lined autoclave under nitrogen pressure (300 psig) while stirring. After 4 days, the mixture (pH=8.0) was cooled, centrifuged, filtered, and washed with water. After drying (110° C. for 2 hr), the product was recovered as a white powder (15.5 g) which showed the following X-ray diffraction pattern:

| PEAK | D-SPACE | RELATIVE INTENSITY |
|---|---|---|
| 1 | 20.575 | 0.1 |
| 2 | 15.445 | 1.4 |
| 3 | 14.918 | 3.4 |
| 4 | 13.755 | 100.0 |
| 5 | 7.155 | 0.4 |
| 6 | 6.889 | 32.6 |
| 7 | 5.345 | 0.8 |
| 8 | 5.085 | 0.1 |
| 9 | 4.593 | 16.9 |
| 10 | 4.216 | 1.0 |
| 11 | 4.138 | 2.1 |
| 12 | 4.130 | 2.1 |
| 13 | 4.034 | 2.0 |
| 14 | 4.023 | 1.7 |
| 15 | 3.833 | 0.8 |
| 16 | 3.721 | 1.8 |
| 17 | 3.711 | 1.3 |
| 18 | 3.660 | 1.4 |
| 19 | 3.552 | 1.0 |
| 20 | 3.271 | 1.0 |
| 21 | 3.189 | 3.1 |
| 22 | 3.105 | 2.9 |
| 23 | 3.101 | 3.2 |
| 24 | 3.097 | 3.2 |
| 25 | 3.038 | 0.3 |
| 26 | 3.003 | 1.5 |
| 27 | 2.998 | 1.8 |
| 28 | 2.951 | 1.0 |
| 29 | 2.837 | 0.5 |
| 30 | 2.824 | 0.9 |
| 31 | 2.816 | 0.6 |
| 32 | 2.756 | 0.7 |
| 33 | 2.670 | 1.3 |

| PEAK | D-SPACE | RELATIVE INTENSITY |
|---|---|---|
| 34 | 2.657 | 0.6 |
| 35 | 2.619 | 2.2 |
| 36 | 2.603 | 0.4 |

These data show that little gain in interstitial spacing is obtained between 25 mol.% and 100 mol.% PPA in the barium preparation. However, the weak intensity in the low angle peak (d=15.89) and the strong intensity of higher angle peaks indicate that a fully pillared material may require higher than 25 mol.% PPA.

EXAMPLE 12

Beryllium oxide powder (6.0 g) was added to a solution of ortho-phosphoric acid (20.9 g) and phenylphosphonic acid (9.48 g) in water (55 g) while the mixture was hand stirred (exothermic). The thin, acidic mixture was adjusted from pH=1 to pH=7.2 with dipropylamine (30.45 g) and heated to 186° C. in a teflon-lined autoclave under nitrogen pressure (205 psig) while stirring. After 4 days, the mixture (pH=7-8) was cooled, centrifuged, filtered, and washed with water. After drying (110° C. for 2 hr), the product was recovered as a white powder 4.7 g) which showed the following X-ray diffraction pattern:

| PEAK | D-SPACE | RELATIVE INTENSITY |
|---|---|---|
| 1 | 16.692 | 100.0 |
| 2 | 15.979 | 1.0 |
| 3 | 5.577 | 1.2 |
| 4 | 4.324 | 1.9 |
| 5 | 4.184 | 9.6 |
| 6 | 4.111 | 1.2 |
| 7 | 3.931 | 1.5 |
| 8 | 3.844 | 0.8 |
| 9 | 3.347 | 1.1 |
| 10 | 2.979 | 0.5 |
| 11 | 2.911 | 0.5 |

EXAMPLE 13

Strontium oxide powder (6.22 g) was added to a solution of ortho-phosphoric acid (5.2 g) and phenylphosphonic acid (2.4 g) in water (55 g) while the mixture was hand stirred (exothermic). The acidic mixture was adjusted from pH=3 to pH=7.2 with dipropylamine (1.73 g) and heated to 174° C. in a teflon-lined autoclave under nitrogen pressure (200 psig) while stirring. After 4 days, the mixture (pH=7.0) was cooled, centrifuged, filtered and washed with water. After drying (110° C. for 2 hr), the product was recovered as a white powder (7.8 g) which showed the following X-ray diffraction pattern:

| PEAK | D-SPACE | RELATIVE INTENSITY |
|---|---|---|
| 1 | 7.014 | 8.0 |
| 2 | 5.075 | 8.3 |
| 3 | 4.256 | 7.6 |
| 4 | 3.778 | 7.0 |
| 5 | 3.643 | 5.6 |
| 6 | 3.500 | 100.0 |
| 7 | 3.482 | 76.8 |
| 8 | 3.349 | 5.8 |
| 9 | 3.222 | 7.9 |
| 10 | 3.049 | 80.5 |
| 11 | 3.004 | 32.8 |
| 12 | 2.944 | 28.3 |
| 13 | 2.928 | 29.9 |
| 14 | 2.863 | 40.2 |
| 15 | 2.840 | 57.5 |
| 16 | 2.626 | 13.5 |

EXAMPLE 14

Strontium oxide powder (6.22 g) was added to a solution of phenylphosphonic acid (9.49 g) in water (55 g) while the mixture was hand stirred (exothermic). The acidic mixture (pH=2.0) was neutralized with dipropylamine (3.29 g; pH=7.2), then heated to 185° C. in a teflon-lined autoclave under nitrogen pressure (200 psig) while stirring. After 2 days, the mixture (pH=8.0) was cooled, centrifuged, filtered, and washed with water. After drying (110° C. for 2 hr), the product was recovered as a white powder (4.5 g) which showed the following X-ray diffraction pattern:

| PEAK | D-SPACE | RELATIVE INTENSITY |
|---|---|---|
| 1 | 15.549 | 18.4 |
| 2 | 14.390 | 22.5 |
| 3 | 14.350 | 100.0 |
| 4 | 7.790 | 1.2 |
| 5 | 7.770 | 1.5 |
| 6 | 7.253 | 3.4 |
| 7 | 7.151 | 21.7 |
| 8 | 6.959 | 0.4 |
| 9 | 5.404 | 2.9 |
| 10 | 5.176 | 1.1 |
| 11 | 5.170 | 1.2 |
| 12 | 4.765 | 9.4 |
| 13 | 4.517 | 0.6 |
| 14 | 4.122 | 1.3 |
| 15 | 3.976 | 0.4 |
| 16 | 3.823 | 1.1 |
| 17 | 3.781 | 1.0 |
| 18 | 3.689 | 3.3 |
| 19 | 3.658 | 1.1 |
| 20 | 3.654 | 0.6 |
| 21 | 3.602 | 0.9 |
| 22 | 3.547 | 2.0 |
| 23 | 3.543 | 3.0 |
| 24 | 3.509 | 0.9 |
| 25 | 3.462 | 3.2 |
| 26 | 3.455 | 2.8 |
| 27 | 3.345 | 0.6 |
| 28 | 3.258 | 1.0 |
| 29 | 3.194 | 3.6 |
| 30 | 3.157 | 0.5 |
| 31 | 3.049 | 1.6 |
| 32 | 3.019 | 1.5 |
| 33 | 2.964 | 1.1 |
| 34 | 2.962 | 1.5 |
| 35 | 2.955 | 0.8 |
| 36 | 2.917 | 0.9 |
| 37 | 2.871 | 0.5 |
| 38 | 2.857 | 1.4 |
| 39 | 2.843 | 1.3 |
| 40 | 2.750 | 4.2 |
| 41 | 2.750 | 3.4 |
| 42 | 2.702 | 0.9 |
| 43 | 2.699 | 1.0 |
| 44 | 2.692 | 0.9 |
| 45 | 2.655 | 1.5 |
| 46 | 2.609 | 0.6 |
| 47 | 2.599 | 1.2 |
| 48 | 2.595 | 0.7 |

EXAMPLE 15

Magnesium oxide powder (9.65 g) is added to a solution of ortho-phosphoric acid (OPA) (20.9 g) and phenylphosphate, (an inorganic-substituted phosphonate) (10.44 g) in water (55 g) while the mixture was hand stirred (exothermic). The ratio of phenylphosphate to OPA was about 1 to 3. The acidic, sudsy mixture is then adjusted from pH=3 to pH=7.2 with dipropylamine (10.9 g) and heated to 180° C. in a teflon-lined autoclave under nitrogen pressure (230 psig) while stirring. After 4 days, the mixture (pH =6.2) is cooled, centrifuged, filtered, and washed with water. After drying (110° C. for 2 hr), the product is recovered as a white powder which shows a d-spacing greater than 14 angstroms.

EXAMPLE 16

Magnesium oxide powder (9.65 g) is added to a solution of arsenic (V) oxide $As_2O_5$ (AO)(20.8 g) and phenylarsonic acid (PAA)

(12.12 g) in water (55 g) while the mixture is hand stirred (exothermic). The ratio of PAA to AO is about 1 to 3. The acidic, sudsy mixture is adjusted from pH=3 to pH=7.2 with dipropylamine (10.9 g) and heated to 180° C. in a teflon-lined autoclave under nitrogen pressure (230 psig) while stirring. After 4 days, the mixture (pH=6.2) is cooled, centrifuged, filtered, and washed with water. After drying (110° C. for 2 hr), the product is recovered as a white powder which shows a d-spacing greater than 14 angstroms.

I claim:

1. A method for preparing a layered divalent metal phosphate-type composition having the formula $M(HAO_4)_x(RAO_3)_y(Z)_z$ wherein M is a divalent metal, A is a pentavalent atom, R is a substituent group other than H or OH, covalently bonded to A, Z is an intercalated moiety, $x+y=1$, y is greater than 0, and z ranges from 0 to 2, said method comprising hydrothermally treating an aqueous reaction mixture having an initial pH prior to said treatment ranging from about 3 to 10 and containing a source of divalent metal, M, and at least one acid of the formula $((HO)_2OA)R$ having a phosphonate structure, wherein A is a pentavalent atom, and R is a ligand other than H and OH, said reaction mixture having a molar ratio of M:A of about 0.8 to 1.2.

2. The method of claim 1 wherein said reaction mixture contains $(HO)_3OA$ wherein A is a pentavalent atom.

3. The method of claim 2 wherein said reaction mixture has a molar ratio of $((HO)_2OA)R:(HO)_3OA$ of at least 1:9.

4. The method of claim 3 wherein said reaction mixture has a molar ratio of $((HO)_2OA)R:(HO)_3OA$ of at least 1:3.

5. The method of claim 1 wherein A is P.

6. The method of claim 2 wherein A is P, and R is selected from the group consisting of acyclic, heteroacyclic, alicyclic, aromatic and heterocyclic groups.

7. The method of claim 6 wherein R is phenyl.

8. The method of claim 5 wherein R is selected from the group consisting of alkoxy, aryloxy, amino, organosilyl, and thionyl.

9. The method of claim 8 wherein M is selected from the group consisting of Be, Mg, Ca, Sr, Ba, Ra, Zn, Cd and Hg.

10. The method of claim 1 wherein said M is Mg.

11. The method of claim 1 wherein said initial pH ranges between about 5 and 9.

12. The method of claim 10 wherein said source of Mg is selected from the group consisting of magnesium oxide and magnesium hydroxide.

13. The method of claim 1 wherein said initial pH ranges from about 6 to 8.

14. The method of claim 13 wherein a pH-raising material is added to said aqueous mixture prior to said hydrothermal treatment.

15. The method of claim 14 wherein said pH-raising material is selected from the group consisting of amines and organic ammonium ions.

16. The method of claim 15 wherein said pH-raising material is selected from the group consisting of dipropylamine, triethylamine and tetraethylammonium hydroxide.

17. The method of claim 1 wherein said hydrothermal treatment conditions include a temperature ranging between about 0° to 50° C., a pressure ranging between about 100 to 345 kPa, and a contact time ranging between about 3 to 72 hours.

18. The method of claim 1 wherein a pH-raising material is added to said aqueous mixture.

19. The method of claim 1 wherein said hydrothermal treatment conditions include a temperature ranging between about 100° to 250° C., a pressure ranging between about 100 to 350 kPa, and a contact time ranging between about 3 to 84 hours.

* * * * *